United States Patent
Jaisser et al.

(10) Patent No.: US 9,121,858 B2
(45) Date of Patent: Sep. 1, 2015

(54) METHODS AND KITS FOR DETECTING CARDIAC REMODELING IN SUBJECTS WITHOUT CLINICAL SIGNS OF HEART FAILURE

(71) Applicants: Institut National de la Sante et de la Recherche Medicale (INSERM), Paris (FR); UNIVERSITE DE LORRAINE, Nancy Cedex (FR); CHU DE NANCY, Nancy (FR)

(72) Inventors: Frederic Jaisser, Paris (FR); Patrick Rossignol, Vandoeuvre les Nancy (FR); Faiez Zannad, Vandoeuvre les Nancy (FR)

(73) Assignees: Institute National de la Sante et de la Recherche Medicale (INSERM), Paris (FR); Universite de Lorraine, Nancy Cedex (FR); Centre Hospaitalier et de Nancy (CHU), Nancy Cedex (FR); Universite Paris Descartes, Paris (FR)

( * ) Notice: Subject to any disclaimer, the term of this patent is extended or adjusted under 35 U.S.C. 154(b) by 0 days.

(21) Appl. No.: 14/351,579

(22) PCT Filed: Oct. 12, 2012

(86) PCT No.: PCT/EP2012/070268
§ 371 (c)(1),
(2) Date: Apr. 14, 2014

(87) PCT Pub. No.: WO2013/053894
PCT Pub. Date: Apr. 18, 2013

(65) Prior Publication Data
US 2014/0249121 A1 Sep. 4, 2014

(30) Foreign Application Priority Data
Oct. 14, 2011 (EP) .................................. 11306335

(51) Int. Cl.
*G01N 33/50* (2006.01)
*C12Q 1/37* (2006.01)
*G01N 33/68* (2006.01)

(52) U.S. Cl.
CPC ........ *G01N 33/6893* (2013.01); *G01N 33/5091* (2013.01); *C12Q 1/37* (2013.01); *G01N 2333/96494* (2013.01); *G01N 2800/32* (2013.01)

(58) Field of Classification Search
None
See application file for complete search history.

(56) References Cited

U.S. PATENT DOCUMENTS

2014/0248284 A1* 9/2014 Zannad et al. ............. 424/158.1
2015/0005260 A1* 1/2015 Zannad et al. .................. 514/91

OTHER PUBLICATIONS

Houard et al., "Mediators of neutrophil recruitment in human abdominal aortic aneurysms", Cardiovascular Research, Jun. 1, 2009, pp. 532-541, vol. 82, No. 3.
Folkesson et al., "Presence of NGAL/MMP-9 complexes in human abdominal aortic aneurysms", Thrombosis and Haemostasis, Aug. 1, 2007, pp. 427-433, vol. 98, No. 2, Chattauer GmbH, DE.

* cited by examiner

*Primary Examiner* — Rosanne Kosson
*Assistant Examiner* — Aaron J Kosar
(74) *Attorney, Agent, or Firm* — Whitham Curtis Christofferson & Cook, PC

(57) ABSTRACT

The present relates to a method for detecting cardiac remodeling in a subject without clinical signs of heart failure comprising determining the level of the NGAL-MMP9 complex in a blood sample obtained from the patient.

5 Claims, 1 Drawing Sheet

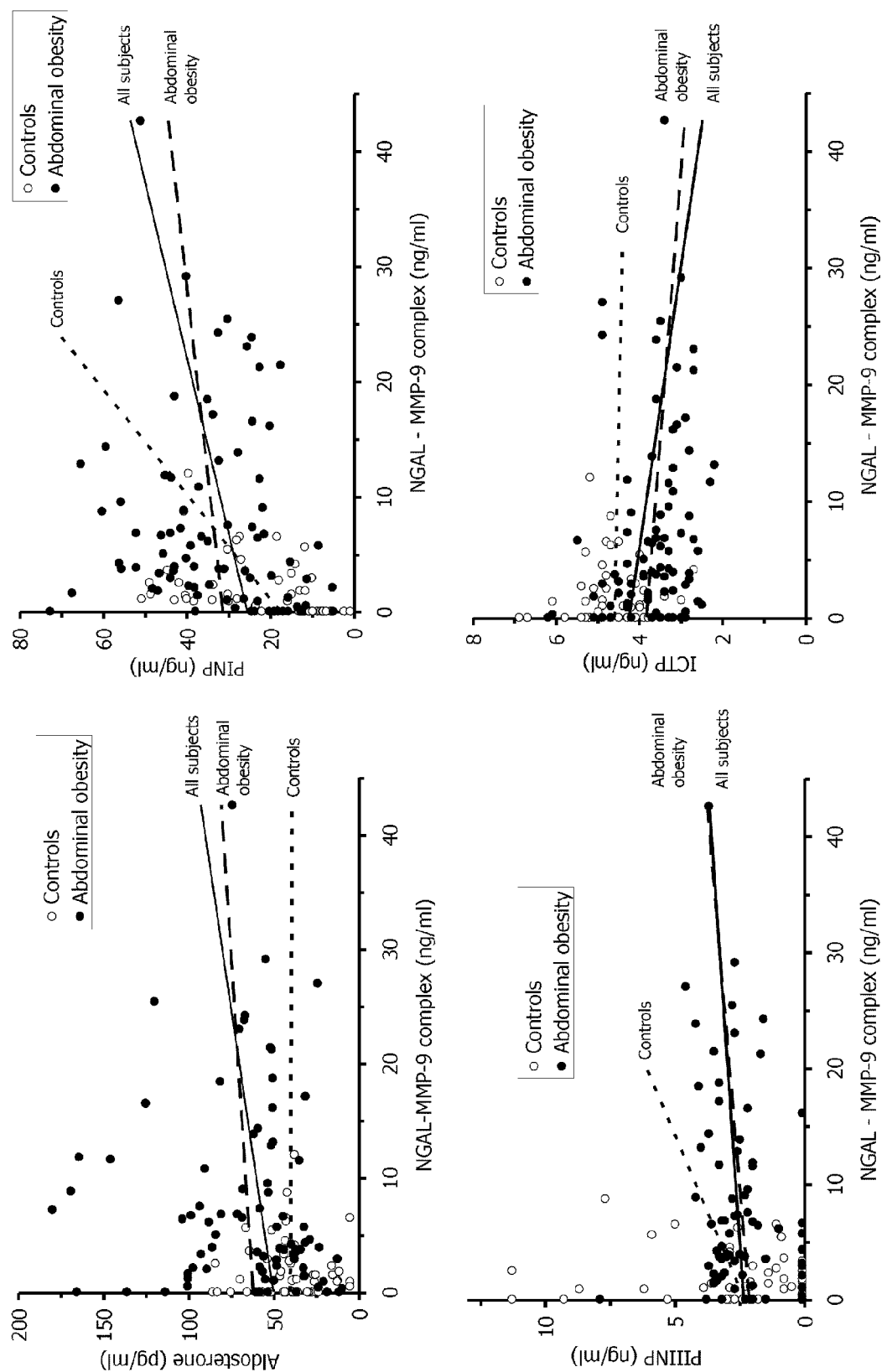

METHODS AND KITS FOR DETECTING CARDIAC REMODELING IN SUBJECTS WITHOUT CLINICAL SIGNS OF HEART FAILURE

FIELD OF THE INVENTION

The present invention relates to methods and kits for detecting cardiac remodeling in subjects without clinical signs of heart failure.

BACKGROUND OF THE INVENTION

Heart failure (HF) is a major and growing public health problem in the United States. Approximately 5 million patients in this country have HF, and over 550,000 patients are diagnosed with HF for the first time each year. Heart failure is the primary reason for 12 to 15 million office visits and 6.5 million hospital days each year.

Heart failure is a complex clinical syndrome that can result from any structural or functional cardiac disorder that impairs the ability of the ventricle to fill with or eject blood. The cardinal manifestations of HF are dyspnea and fatigue (which may limit exercise tolerance) and fluid retention (which may lead to pulmonary congestion and peripheral edema). Both abnormalities can impair the functional capacity and quality of life of affected subjects.

Heart failure may result from disorders of the pericardium, myocardium, endocardium or great vessels, but the majority of patients with HF have symptoms due to an impairment of left ventricular (LV) myocardial function. LV myocardial dysfunction begins with some injury to, or stress on, the myocardium and is generally a progressive process, even in the absence of a new identifiable insult to the heart. The principal manifestation of such progression is a change in the geometry and structure of the LV, such that the chamber dilates and/or hypertrophies and becomes more spherical, a process referred to as cardiac remodeling. This change in chamber size and structure not only increases the hemodynamic stresses on the walls of the failing heart and depresses its mechanical performance but may also increase regurgitant flow through the mitral valve. These effects, in turn, serve to sustain and exacerbate the remodeling process. Cardiac remodeling generally precedes the development of symptoms (sometimes by months or even years), continues after the appearance of symptoms, and contributes substantially to worsening of symptoms despite treatment.

Accordingly, methods and kits for detecting early cardiac remodeling in subjects without clinical signs of heart failure are highly desirable, especially in subjects at risk such as obese subjects.

SUMMARY OF THE INVENTION

The present invention relates to a method for detecting cardiac remodeling in a subject without clinical signs of heart failure comprising determining the level of the NGAL-MMP9 complex in a blood sample obtained from the patient.

DETAILED DESCRIPTION OF THE INVENTION

Within a cross-sectional study of normotensive obese participants without left ventricular hypertrophy and without HF signs (i.e HF Stage A) compared to healthy volunteers, the inventors observed that plasma Aldo levels, although still in the normal range, were correlated to cardiovascular fibrosis, as assessed by circulating biomarkers of cardiac extracellular matrix. Interestingly, in this setting NGAL-MMP-9 was found significantly associated with both plasma Aldo levels, and cardiac fibrosis biomarkers. This suggests that NGAL-MMP-9 was already altered at the early stage of cardiac remodeling that precedes clinical HF, and may therefore be a key-factor in the Aldo signaling pathway leading to tissue remodeling and heart failure.

Accordingly, the present invention relates to a method for detecting cardiac remodeling in a subject without clinical signs of heart failure comprising determining the level of the NGAL-MMP9 complex in a blood sample obtained from the patient.

As used herein, the phrase, "cardiac remodeling" refers to a compensatory physiologic response to an event or condition that compromises cardiac function. Triggers for cardiac remodeling include myocardial infarction, hypertension, wall stress, inflammation, pressure overload, and volume overload. Alterations in myocardial structure can occur as quickly as within a few hours of injury, and may progress over months and years. Thus, the phrase "cardiac remodeling" encompasses the global, cellular, and genetic changes that lead to alterations in the ventricular shape and function. While initially beneficial, these changes over time (months to years) can impair myocardial function to the point of chronic intractable heart failure. The hallmarks of cardiac remodeling are manifested as chamber dilation, increase in ventricular sphericity, and the development of interstitial and perivascular fibrosis. Increased sphericity is positively associated with mitral regurgitation. Ventricular dilation mainly results from cardiomyocyte hypertrophy and lengthening, and to a lesser extent from increases in the ventricular mass.

In a particular embodiment, the method of the invention is particularly suitable for detecting cardiac remodeling mediated by aldosterone.

As used herein, the phrase "heart failure", refers to any condition that can result from any structural or functional cardiac disorder that impairs the ability of the heart (e.g., the ventricle) to fill with or eject blood.

Typically a subject without clinical signs of heart failure is a subject classified at stage A of heart failure. The development of HF can be indeed characterized by considering 4 stages of the disease. The first stage, Stage A, is a subject at high risk for HF but without structural heart disease, clinical signs or symptoms of HF (for example, these are patients with hypertension, atherosclerotic disease, diabetes, obesity, metabolic syndrome or patients using cardiotoxins). The second stage, Stage B, is a subject having structural heart disease but without signs or symptoms of HF (for example, these are patients who have previously had obesity, exhibit LV remodeling including LV hypertrophy). The third stage, Stage C, is a subject having structural heart disease with prior or current symptoms of HF (for example, these are patients who have known structural heart disease and exhibit shortness of breath and fatigue and have reduced exercise tolerance). The fourth and final stage, Stage D, is refractory HF requiring specialized interventions (for example, patients who have marked symptoms at rest despite maximal medical therapy (namely, those who are recurrently hospitalized or cannot be safely discharged from the hospital without specialized interventions).

In a particular embodiment, the subject is an obese subject, and preferably a subject with abdominal obesity (>94 cm for male and >80 cm for female).

By "blood sample" is meant a volume of whole blood or fraction thereof, eg, serum, plasma, etc.

The term "Lipocalin 2" or "NGAL" has its general meaning in the art and refers to the Neutrophil Gelatinase-Associated Lipocalin as described in Schmidt-Ott K M. et al. (2007). NGAL is a glycoprotein and was originally identified as a neutrophil specific granule component and a member of the lipocalin family of proteins. The protein may be covalently complexed with neutrophil gelatinase (also known as matrix metalloproteinase 9, "MMP-9") via an intermolecular disulphide bridge as a 135-kDa heterodimeric form ("NGAL-MMP9 complex").

Methods for determining the level of a biomarker protein such as NGAL-MMP9 complex in a blood sample are well known in the art.

In a particular embodiment, the methods of the invention comprise contacting the blood sample with a binding partner capable of selectively interacting with the biomarker protein present in the blood sample. The binding partner may be an antibody that may be polyclonal or monoclonal, preferably monoclonal. In another embodiment, the binding partner may be an aptamer.

According to the invention, the binding partner is specific for the NGAL-MMP9 complex, namely has a higher affinity for the NGAL-MMP9 complex than for NGAL or MMP9 alone. Preferably the cross reaction between the NGAL-MMP9 and NGAL or MMP9 is low even null. Typically, the affinity of the binding partner is at least 10, preferably 100, more preferably 1000 or even more preferably 10000 higher that the affinity for NGAL or MMP9 alone.

The skilled man in the art can easily discriminates binding partners specific for the NGAL-MMP9 complex that those non specific for said complex. Epitope binning can be used to identify binding partners that fall within the scope of the claimed invention. Epitope binning refers to the use of competitive binding assays to identity binding partners that are, or are not capable of binding NGAL-MMP9 complex simultaneously with NGAL or MMP9, thereby identifying binding partners that bind to epitopes on NGAL-MMP9 that are not retrived in NGAL or MMP9. Epitope binning experiments provide evidence that antigenically distinct epitopes are present. The binding partners and typically antibodies of the present invention may be assayed for specific binding by any method known in the art. Many different competitive binding assay format(s) can be used for epitope binning The immunoassays which can be used include, but are not limited to, competitive assay systems using techniques such western blots, radioimmunoassays, ELISA, "sandwich" immunoassays, immunoprecipitation assays, precipitin assays, gel diffusion precipitin assays, immunoradiometric assays, fluorescent immunoassays, protein A immunoassays, and complement-fixation assays. Such assays are routine and well known in the art (see, e.g., Ausubel et al., eds, 1994 Current Protocols in Molecular Biology, Vol. 1, John Wiley & sons, Inc., New York). For example, the BIACORE® (GE Healthcare, Piscataway, N.J.) is one of a variety of surface plasmon resonance assay formats that are routinely used to epitope bin panels of monoclonal antibodies. Additionally, routine cross-blocking assays such as those described in Antibodies, A Laboratory Manual, Cold Spring Harbor Laboratory, Ed Harlow and David Lane, 1988, can be performed.

Polyclonal antibodies of the invention or a fragment thereof can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred.

Monoclonal antibodies of the invention or a fragment thereof can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985).

Alternatively, techniques described for the production of single chain antibodies (see e.g. U.S. Pat. No. 4,946,778) can be adapted to produce anti-NGAL-MMP9 complex, single chain antibodies. Antibodies useful in practicing the present invention also include anti-NGAL-MMP9 complex fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to NGAL-MMP9 complex. For example, phage display of antibodies may be used. In such a method, single-chain Fv (scFv) or Fab fragments are expressed on the surface of a suitable bacteriophage, e. g., M13. Briefly, spleen cells of a suitable host, e. g., mouse, that has been immunized with a protein are removed. The coding regions of the VL and VH chains are obtained from those cells that are producing the desired antibody against the protein. These coding regions are then fused to a terminus of a phage sequence. Once the phage is inserted into a suitable carrier, e. g., bacteria, the phage displays the antibody fragment. Phage display of antibodies may also be provided by combinatorial methods known to those skilled in the art. Antibody fragments displayed by a phage may then be used as part of an immunoassay.

In another embodiment, the binding partner may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. 1997. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consist of conformationally constrained antibody variable regions displayed by a platform protein, such as *E. coli* Thioredoxin A, that are selected from combinatorial libraries by two hybrid methods (Colas et al., 1996).

The binding partners of the invention such as antibodies or aptamers, may be labelled with a detectable molecule or substance, such as a fluorescent molecule, a radioactive molecule or any others labels known in the art. Labels are known in the art that generally provide (either directly or indirectly) a signal.

As used herein, the term "labelled", with regard to the antibody, is intended to encompass direct labelling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labelling of the probe or antibody by reactivity with a detectable substance. An antibody or aptamer of the invention may be labelled with a radioactive molecule by any method known in the art. For example radioactive molecules include but are not limited radioactive atom for scintigraphic studies such as I123, I124, In111, Re186, Re188.

The afore mentioned assays generally involve the binding of the binding partner (ie. antibody or aptamer) to a solid support. Solid supports which can be used in the practice of the invention include substrates such as nitrocellulose (e. g., in membrane or microtiter well form); polyvinylchloride (e. g., sheets or microtiter wells); polystyrene latex (e.g., beads or microtiter plates); polyvinylidine fluoride; diazotized paper; nylon membranes; activated beads, magnetically responsive beads, and the like.

The level of biomarker protein may be measured by using standard immunodiagnostic techniques, including immunoassays such as competition, direct reaction, or sandwich type assays. Such assays include, but are not limited to, agglutination tests; enzyme-labelled and mediated immunoassays, such as ELISAs; biotin/avidin type assays; radioimmunoassays; immunoelectrophoresis; immunoprecipitation.

More particularly, an ELISA method can be used, wherein the wells of a microtiter plate are coated with a set of antibodies which recognize said biomarker protein. A blood sample containing or suspected of containing said biomarker protein is then added to the coated wells. After a period of incubation sufficient to allow the formation of antibody-antigen complexes, the plate(s) can be washed to remove unbound moieties and a detectably labelled secondary binding molecule added. The secondary binding molecule is allowed to react with any captured sample marker protein, the plate washed and the presence of the secondary binding molecule detected using methods well known in the art.

Measuring the level of the biomarker protein (with or without immunoassay-based methods) may also include separation of the compounds: centrifugation based on the compound's molecular weight; electrophoresis based on mass and charge; HPLC based on hydrophobicity; size exclusion chromatography based on size; and solid-phase affinity based on the compound's affinity for the particular solid-phase that is used. Once separated, said biomarker protein may be identified based on the known "separation profile" e. g., retention time, for that compound and measured using standard techniques.

Alternatively, the separated compounds may be detected and measured by, for example, a mass spectrometer.

In a particular embodiment, the method of the invention further comprises a step consisting of comparing the determined level of NGAL-MMP9 complex in the blood sample obtained from the subject with a reference level, wherein a difference between said determined level and said reference level is indicative that cardiac remodeling, especially of cardiac remodeling mediated (but not exclusive to) by aldosterone, is present in said subject.

In one embodiment, the reference values may be index values or may be derived from one or more risk prediction algorithms or computed indices for cardiac remodeling. A reference value can be relative to a number or value derived from population studies, including without limitation, such subjects having similar body mass index, similar abdominal obesity, total cholesterol levels, LDL/HDL levels, systolic or diastolic blood pressure, subjects of the same or similar age range, subjects in the same or similar ethnic group . . . . In one embodiment of the present invention, the reference value is derived from the level of NGAL-MMP9 complex in a control sample derived from one or more subjects who are substantially healthy (i.e. having no cardiac remodeling or obesity). In another embodiment, such subjects are monitored and/or periodically retested for a diagnostically relevant period of time ("longitudinal studies") following such test to verify continued absence of cardiac remodeling. Such period of time may be one year, two years, two to five years, five years, five to ten years, ten years, or ten or more years from the initial testing date for determination of the reference value. Furthermore, retrospective measurement of NGAL-MMP9 complex levels in properly banked historical subject samples may be used in establishing these reference values, thus shortening the study time required, presuming the subjects have been appropriately followed during the intervening period through the intended horizon of the product claim. Typically, the levels of NGAL-MMP9 complex in a subject has cardiac remodeling is deemed to be higher than the reference value obtained from healthy subjects who have developed cardiac remodeling.

The method of the invention is particularly suitable for the management and the appreciation of risk for heart failure. Accordingly, the present invention relates to a method for determining whether a subject is at risk of developing heart failure comprising a step consisting of detecting cardiac remodeling according to the method as above described.

According to the invention, when cardiac remodeling is detected by the method of the invention, then the subject may be administered with a mineralocorticoid antagonist. Mineral antagonists are well known in the art and include but are not limited to spirolactone-type steroidal compounds (such as spironolactone or eplerenone) or non steroidal compounds (Meyers, Marvin J1; Hu, Xiao Expert Opinion on Therapeutic Patents, Volume 17, Number 1, January 2007, pp. 17-23(7)).

Yet another object of the invention relates to a kit for performing a method of the invention, said kit comprising means for measuring the level of NGAL-MMP9 complex in a blood sample obtained from the subject. Typically the kit may include an antibody, or a set of antibodies as above described. In a particular embodiment, the antibody or set of antibodies are labelled as above described. The kit may also contain other suitably packaged reagents and materials needed for the particular detection protocol, including solid-phase matrices, if applicable, and standards. The kit may also contain one or more means for the detection of a further biomarker. Typically the kit may also contain means for the detection of one ore more heart failure biomarker selected from the group consisting of brain natriuretic peptide (BNP), amino-terminal pro-brain natriuretic peptide (NT-pro BNP), norepinephrine, troponin, heart-type fatty acid binding protein, myosin light chain-1, matrix metalloproteinase, tissue inhibitor of matrix metalloproteinase, C-reactive protein (CRP), TNFalpha, soluble tumor necrosis factor receptor 1 (sTNFR1), soluble T2 receptor, soluble IL-2 receptor, CD40-CD154, CCAM-I, P-selectin, tissue factor and von Willebrand factor, urocortin, myeloperoxidase, and uric acid.

The invention will be further illustrated by the following figures and examples. However, these examples and figures should not be interpreted in any way as limiting the scope of the present invention.

FIGURES

FIG. 1: Correlation plots between NGAL-MMP-9 and aldosterone or collagen peptides in controls and obese subjects, and in the whole population. Correlation coefficients and 95% confidence intervals from non-parametric Spearman's analysis are indicated. Straight lines are the usual unadjusted regression lines (parametric analysis; continuous: all subjects, small dots: controls, large dots: abdominal obesity).

EXAMPLE

Methods

Asymptomatic subjects (40-65 years) with abdominal obesity (AO) (>94 cm for male, >80 cm for female (Holt R I. International diabetes federation re-defines the metabolic syndrome. Diabetes Obes Metab. 2005; 7:618-620) and age-gender matched healthy volunteers (BMI <25 kg/m$^2$) without AO were recruited through press advertisement. Known diabetic subjects, or participants with known or suspected hypertension at the screening visit (ie blood pressure>140/90 mm Hg), morbid obesity (body mass index>40 kg/m$^2$), personal history of cardiovascular events or of endocrine disease, inflammatory or neoplasic diseases were excluded. Written informed consent was obtained. The study was approved by the local ethics committee (CPP Est-III) and all subjects provided written informed consent.

Cardiovascular and biological phenotyping included blood pressure measurements and Magnetic Resonance Imaging (MRI) to determine left ventricular mass (see infra). In addition to plasma measurements (see infra), free NGAL (DM9L20, R&D Systems) and NGAL-MMP-9 complexes (NGAL20, R&D Systems) were assessed using ELISA and total NGAL was computed as the sum of free and NGAL-MMP-9. Radioimmunoassay kits (Orion Diagnostica, Espoo, Finland) were used for determinations of serum collagen peptides (PINP: aminoterminal propeptide of type I procollagen, aminoterminal propeptide of PIIINP procollagen type III, ICTP: type 1 collagen telopeptide) as reported (Iraqi W, Rossignol P, Angioi M, Fay R, Nuee J, Ketelslegers J M, Vincent J, Pitt B, Zannad F. Extracellular cardiac matrix biomarkers in patients with acute myocardial infarction complicated by left ventricular dysfunction and heart failure: Insights from the eplerenone post-acute myocardial infarction heart failure efficacy and survival study (ephesus) study. Circulation. 2009; 119:2471-2479). The same operator performed these tests, blinded for subjects group.

MRI was performed on a 1.5-T magnet (Signa Excite, GE Medical Systems, Milwaukee, Wis., USA) equipped with an 8-element phased-array surface coil. Main acquisition parameters were as follows: 8 mm slice-thickness, 3.5-3.9 ms repetition time, 14 to 16 K-space lines per segment, 30 phases per cardiac cycle with view sharing, field-of-view (FOV) ranging from 32 to 38 cm with a phase FOV of 0.9, and a 224×224 matrix. The left ventricular mass was determined on the contiguous SSFP short-axis slices, using dedicated software (MASS™, Medis, The Netherlands). The left ventricular mass was determined at end-diastole, and papillary muscles and trabeculations were excluded for left ventricular mass measurement (Codreanu A, Djaballah W, Angioi M, et al. Detection of myocarditis by contrast-enhanced MRI in patients presenting with acute coronary syndrome but no coronary stenosis. J Magn Reson Imaging 2007; 25(5):957-964.; Mandry D, Lapicque F, Odille F, et al. Multicompartmental analysis of late contrast enhancement in areas of myocardial infarction supplied by chronically occluded coronary arteries. J Magn Reson Imaging 2009; 29(1):78-85.).

Results

Increased plasma NGAL concentrations have been reported in obese patients (Auguet T, Quintero Y, Terra X, Martinez S, Lucas A, Pellitero S, Aguilar C, Hernandez M, Del Castillo D, Richart C. Upregulation of lipocalin 2 in adipose tissues of severely obese women: Positive relationship with proinflammatory cytokines. Obesity., Wang Y, Lam K S, Kraegen E W, Sweeney G, Zhang J, Tso A W, Chow W S, Wat N M, Xu J Y, Hoo R L, Xu A. Lipocalin-2 is an inflammatory marker closely associated with obesity, insulin resistance, and hyperglycemia in humans. Clin Chem. 2007; 53:34-41, Catalan V, Gomez-Ambrosi J, Rodriguez A, Ramirez B, Silva C, Rotellar F, Gil M J, Cienfuegos J A, Salvador J, Fruhbeck G. Increased adipose tissue expression of lipocalin-2 in obesity is related to inflammation and matrix metalloproteinase-2 and metalloproteinase-9 activities in humans. J Mol Med. 2009; 87:803-813.) a population prone to develop both hyperaldosteronism and HF (Krug A W, Ehrhart-Bornstein M. Adrenocortical dysfunction in obesity and the metabolic syndrome. Horm Metab Res. 2008; 40:515-517; Schinner S, Willenberg H S, Krause D, Schott M, Lamounier-Zepter V, Krug A W, Ehrhart-Bornstein M, Bornstein S R, Scherbaum W A. Adipocyte-derived products induce the transcription of the star promoter and stimulate aldosterone and cortisol secretion from adrenocortical cells through the wnt-signaling pathway. Int J Obes (Lond). 2007; 31:864-870; Engeli S, Bohnke J, Gorzelniak K, Janke J, Schling P, Bader M, Luft F C, Sharma A M. Weight loss and the renin-angiotensin-aldosterone system. Hypertension. 2005; 45:356-362.). In obese subjects without signs of HF, we aimed at determining whether plasma NGAL concentrations may be correlated to serum Aldo levels and to blood levels of biomarkers of cardiovascular fibrosis (PINP: aminoterminal propeptide of type I procollagen, PIIINP: aminoterminal propeptide of procollagen type III, which are biomarkers of collagen synthesis and ICTP: type 1 collagen telopeptide, which is a biomarker of collagen degradation) (Zannad F, Rossignol P, Iraqi W. Extracellular matrix fibrotic markers in heart failure. Heart Fail Rev. 2010; 15:319-329.).

Compared to healthy-volunteers (Table 1), subjects with abdominal obesity (AO), without history of cardiovascular disease, tended to exhibit some features of the metabolic syndrome (but not hypertension). None of the participants exhibited left ventricular hypertrophy, as defined by Alfaki (women: ≥60 g/m$^2$ and men ≥77 g/m$^2$] as assessed by MRI (Alfakih K, Plein S, Bloomer T, Jones T, Ridgway J, Sivananthan M. Comparison of right ventricular volume measurements between axial and short axis orientation using steady-state free precession magnetic resonance imaging. J Magn Reson Imaging. 2003; 18:25-32). AO displayed a 3.7 fold increase in NGAL-MMP-9 (p<0.0001), a 70% increase in plasma Aldo levels (p<0.0001), a 2.1 fold increase in PINP (p<0.0001), and a 23% decrease in ICTP (p<0.0001) (Table 1). No significant correlation was observed between free NGAL or total NGAL and plasma Aldo, or with extracellular matrix biomarkers. In contrast, NGAL-MMP-9 was positively significantly correlated with plasma Aldo, PINP, PIIINP and negatively correlated with ICTP, a correlation mainly driven by the AO group (FIG. 1). Meanwhile, plasma Aldo was found associated with PINP (r=0.17, p=0.046), as well as with ICTP (r=−0.19, p=0.025) in the whole study population.

TABLE 1

Study population features

| | Controls Median (IQR) | Abdominal obesity Median (IQR) | p value |
|---|---|---|---|
| Age (years) | 54 (50-58) | 55 (51-59) | 0.45 |
| Gender male: n (%) | 24 (45) | 39 (46) | 0.95 |
| Weight (kg) | 61 (57-71) | 89 (77-96) | <0.0001 |
| Height (cm) | 1.69 (1.61-1.74) | 1.67 (1.58-1.72) | 0.20 |
| BMI (kg/m$^2$) | 22.5 (21.1-24.0) | 31.4 (29.6-33.4) | <0.0001 |
| Waist circumference (cm) | 78 (70-85) | 102 (96-108) | <0.0001 |
| SBP (mmHg) | 115 (110-123) | 121 (114-130) | 0.006 |
| DBP (mmHg) | 72 (66-76) | 73 (68-79) | 0.25 |

TABLE 1-continued

Study population features

| | Controls Median (IQR) | Abdominal obesity Median (IQR) | p value |
|---|---|---|---|
| MBP (mmHg) | 87 (82-91) | 89 (83-95) | 0.033 |
| Heart rate (bpm) | 60 (57-66) | 70 (62-77) | <0.0001 |
| Total cholesterol (mmol/l) | 5.52 (4.92-5.75) | 5.91 (5.26-6.47) | 0.019 |
| LDL-cholesterol (mmol/l) | 3.37 (3.03-3.99) | 3.63 (3.19-4.10) | 0.14 |
| HDL-cholesterol (mmol/l) | 1.63 (1.35-1.86) | 1.29 (1.14-1.66) | 0.006 |
| Triglycerides (mmol/l) | 0.75 (0.66-1.01) | 1.34 (0.93-1.92) | <0.0001 |
| Blood glucose (mmol/l) | 4.83 (4.44-5.16) | 5.00 (4.72-5.33) | 0.046 |
| C-reactive protein (mg/l) | 0.85 (0.49-1.41) | 2.20 (1.14-4.70) | <0.0001 |
| Estimated GFR (ml/min/1.73 m$^2$) | 76 (67-83) | 78 (68-84) | 0.87 |
| NGAL (ng/ml) | 79.1 (57.0-97.8) | 71.7 (61.2-84.7) | 0.57 |
| NGAL-MMP-9 (ng/ml) | 1.20 (0.10-2.80) | 4.40 (1.90-11.60) | <0.0001 |
| Total NGAL (ng/ml) | 82.2 (58.2-100.2) | 78.2 (70.8-94.6) | 0.75 |
| Aldosterone (pg/ml) | 39.4 (27.1-46.6) | 55.3 (38.2-84.3) | <0.0001 |
| PINP (ng/ml) | 16.0 (10.4-33.9) | 33.9 (23.2-43.8) | <0.0001 |
| PIIINP (ng/ml) | 2.10 (0.10-3.20) | 2.70 (2.00-3.30) | 0.20 |
| ICTP (ng/ml) | 4.50 (4.00-5.10) | 3.50 (3.05-4.25) | <0.0001 |
| Left ventricular mass | | | |
| g | 78 (71-98) | 90 (75-110) | 0.047 |
| g/m2 BSA | 47 (43-52) | 43 (38-52) | 0.061 | p-value from the non parametric Mann-Whitney test for continuous variables, from the Chi-Square test for gender.
BMI, body mass index;
SBP, systolic blood pressure;
DBP, diastolic blood pressure;
MBP, mean blood pressure;
GFR, glomerular filtration rate.

REFERENCES

Throughout this application, various references describe the state of the art to which this invention pertains. The disclosures of these references are hereby incorporated by reference into the present disclosure.

The invention claimed is:

1. A method for detecting cardiac remodeling in a subject without clinical signs of heart failure comprising:
   a) determining the level of neutrophil gelatinase-associated lipocalin:matrix metalloproteinase 9 (NGAL-MMP9) complex in a blood sample obtained from the subject; and
   b) comparing the determined level of the NGAL-MMP9 complex in the blood sample obtained from the subject with a blood NGAL-MMP9 complex reference level from a subject who does not have cardiac remodeling, wherein an increase between said determined level and said reference level is indicative that cardiac remodeling is present in said subject.

2. The method according to claim 1 wherein said subject is a subject with abdominal obesity.

3. The method according to claim 1 wherein said cardiac remodeling is mediated by aldosterone.

4. A method for treating a subject affected with cardiac remodeling without clinical signs of heart failure, comprising the steps of:
   a) determining whether a subject without clinical signs of heart failure is affected by cardiac remodeling by:
      (i) determining the level of neutrophil gelatinase-associated lipocalin:matrix metalloproteinase 9 (NGAL-MMP9) complex in a blood sample obtained from the subject; and
      (ii) comparing the determined level of the NGAL-MMP9 complex in the blood sample obtained from the subject with a blood NGAL-MMP9 complex reference level from a subject who does not have cardiac remodeling, wherein an increase between said determined level and said reference level is indicative that cardiac remodeling is present in said subject; and
   b) administering a mineralocorticoid antagonist to said subject identified as a subject affected with cardiac remodeling.

5. The method according to claim 4 wherein the subject is a subject with abdominal obesity.

* * * * *